United States Patent
Davis et al.

(10) Patent No.: US 10,172,514 B2
(45) Date of Patent: Jan. 8, 2019

(54) CANNULA WITH PROXIMALLY MOUNTED CAMERA AND TRANSPARENT OBTURATOR

(71) Applicant: Rebound Therapeutics Corporation, Irvine, CA (US)

(72) Inventors: Peter G. Davis, Irvine, CA (US); Ross Tsukashima, Irvine, CA (US); Jeffrey J. Valko, Irvine, CA (US); Michael R. Henson, Irvine, CA (US); Todd McIntyre, Irvine, CA (US)

(73) Assignee: Rebound Therapeutics Corporation, Irvine, CA (US)

( * ) Notice: Subject to any disclaimer, the term of this patent is extended or adjusted under 35 U.S.C. 154(b) by 0 days.

(21) Appl. No.: 15/895,295

(22) Filed: Feb. 13, 2018

(65) Prior Publication Data

US 2018/0206714 A1 Jul. 26, 2018

Related U.S. Application Data

(63) Continuation of application No. 15/576,536, filed as application No. PCT/US2017/047424 on Aug. 17, (Continued)

(51) Int. Cl.
  *A61B 1/00* (2006.01)
  *A61B 1/313* (2006.01)
  (Continued)

(52) U.S. Cl.
  CPC .............. *A61B 1/313* (2013.01); *A61B 1/00* (2013.01); *A61B 1/00006* (2013.01);
  (Continued)

(58) Field of Classification Search
  CPC ....... A61B 1/313; A61B 1/05; A61B 1/00009; A61B 1/00045; A61B 1/0669;
  (Continued)

(56) References Cited

U.S. PATENT DOCUMENTS

| 5,004,332 A | 4/1991 | Edwards |
| 5,957,832 A | 9/1999 | Taylor et al. |

(Continued)

FOREIGN PATENT DOCUMENTS

| EP | 2430992 | 3/2012 |
| JP | 201616053 | 2/2016 |

(Continued)

OTHER PUBLICATIONS

Examination Report dated Oct. 25, 2017 from Australian Patent Application No. 2017232046.

(Continued)

*Primary Examiner* — Timothy J Neal

(74) *Attorney, Agent, or Firm* — Crockett & Crockett; K. David Crockett, Esq.

(57) ABSTRACT

A cannula system and method for accessing a blood mass in the brain. The system comprises a cannula with a camera mounted on the proximal end of the cannula with a view into the cannula lumen and the surgical field below the lumen. A prism, reflector or other suitable optical element is oriented between the camera and the lumen of the cannula to afford the camera a view into the cannula while minimizing obstruction of the lumen. The system may also include an obturator with a small diameter shaft and a large diameter tip which is optically transmissive, so that a surgeon inserting or manipulating the assembly can easily see that the obturator tip is near brain tissue (which is white) or blood (which is red).

5 Claims, 9 Drawing Sheets

Related U.S. Application Data 2017, which is a continuation-in-part of application No. 15/239,632, filed on Aug. 17, 2016.

(60) Provisional application No. 62/483,885, filed on Apr. 10, 2017.

(51) Int. Cl.
| | | |
|---|---|---|
| *A61B 17/02* | (2006.01) | |
| *A61B 1/05* | (2006.01) | |
| *A61B 90/00* | (2016.01) | |
| *A61B 17/34* | (2006.01) | |
| *A61B 1/06* | (2006.01) | |
| *A61B 1/04* | (2006.01) | |
| *A61B 34/20* | (2016.01) | |
| *A61B 90/10* | (2016.01) | |
| *A61B 17/00* | (2006.01) | |
| *A61B 90/30* | (2016.01) | |
| *A61B 34/10* | (2016.01) | |

(52) U.S. Cl.
CPC ...... *A61B 1/00009* (2013.01); *A61B 1/00045* (2013.01); *A61B 1/00147* (2013.01); *A61B 1/00188* (2013.01); *A61B 1/00195* (2013.01); *A61B 1/04* (2013.01); *A61B 1/05* (2013.01); *A61B 1/06* (2013.01); *A61B 1/0669* (2013.01); *A61B 17/02* (2013.01); *A61B 17/0218* (2013.01); *A61B 17/34* (2013.01); *A61B 17/3421* (2013.01); *A61B 17/3423* (2013.01); *A61B 34/20* (2016.02); *A61B 90/00* (2016.02); *A61B 90/361* (2016.02); *A61B 17/3417* (2013.01); *A61B 90/10* (2016.02); *A61B 2017/00907* (2013.01); *A61B 2017/00991* (2013.01); *A61B 2017/3425* (2013.01); *A61B 2017/3433* (2013.01); *A61B 2017/3454* (2013.01); *A61B 2034/107* (2016.02); *A61B 2090/103* (2016.02); *A61B 2090/309* (2016.02); *A61B 2090/3937* (2016.02); *A61B 2090/3966* (2016.02)

(58) Field of Classification Search
CPC ............ A61B 1/00195; A61B 1/00006; A61B 1/00188; A61B 17/3423; A61B 2017/3423; A61B 2017/00907; A61B 2017/3425; A61B 2017/3454
See application file for complete search history.

(56) References Cited

U.S. PATENT DOCUMENTS

| | | | | |
|---|---|---|---|---|
| 6,152,871 | A | * | 11/2000 | Foley ............... A61B 17/3417 600/102 |
| 6,361,488 | B1 | * | 3/2002 | Davison ........... A61B 1/00147 600/102 |
| 9,216,015 | B2 | | 12/2015 | Wilson |
| 2002/0022764 | A1 | | 2/2002 | Smith et al. |
| 2004/0102804 | A1 | | 5/2004 | Chin |
| 2006/0069314 | A1 | | 3/2006 | Farr |
| 2008/0058594 | A1 | | 3/2008 | Xie |
| 2008/0086074 | A1 | * | 4/2008 | Taylor ............... A61B 1/0008 604/26 |
| 2008/0109026 | A1 | | 5/2008 | Kassam |
| 2009/0048622 | A1 | | 2/2009 | Wilson |
| 2009/0318758 | A1 | | 12/2009 | Farr et al. |
| 2010/0013910 | A1 | | 1/2010 | Farr |
| 2010/0063356 | A1 | * | 3/2010 | Smith ............... A61B 1/3132 600/114 |
| 2010/0081988 | A1 | | 4/2010 | Kahle et al. |
| 2011/0087159 | A1 | | 4/2011 | Parihar et al. |
| 2011/0160535 | A1 | | 6/2011 | Bayer et al. |
| 2011/0251456 | A1 | | 10/2011 | Jacobsen et al. |
| 2012/0224263 | A1 | | 9/2012 | Gallagher |
| 2014/0275771 | A1 | | 9/2014 | Henley et al. |
| 2014/0324080 | A1 | | 10/2014 | Wallace |
| 2015/0265369 | A1 | | 9/2015 | Garbey et al. |
| 2015/0366583 | A1 | | 12/2015 | Druma et al. |
| 2016/0045224 | A1 | | 2/2016 | Hendershot, III |

FOREIGN PATENT DOCUMENTS

| | | |
|---|---|---|
| WO | WO2001054560 | 8/2001 |
| WO | WO2009094644 | 7/2009 |
| WO | WO2013092222 | 6/2013 |
| WO | WO2015135057 | 9/2015 |

OTHER PUBLICATIONS

Combined Search and Examination Report dated Sep. 28, 2017 from Great Britain Patent Application No. 1714253.0.
Combined Search and Examination Report dated Sep. 28, 2017 from Great Britain Patent Application No. 1714722.4.
International Search Report and Written Opinion dated Jan. 15, 2018 from International Application No. PCT/US2017/047424.
Office Action dated Jul. 17, 2018 from U.S. Appl. No. 15/895,335.
Office Action dated Jul. 18, 2018 from U.S. Appl. No. 15/239,632.
Office Action dated Jul. 17, 2018 from U.S. Appl. No. 15/895,277.

\* cited by examiner

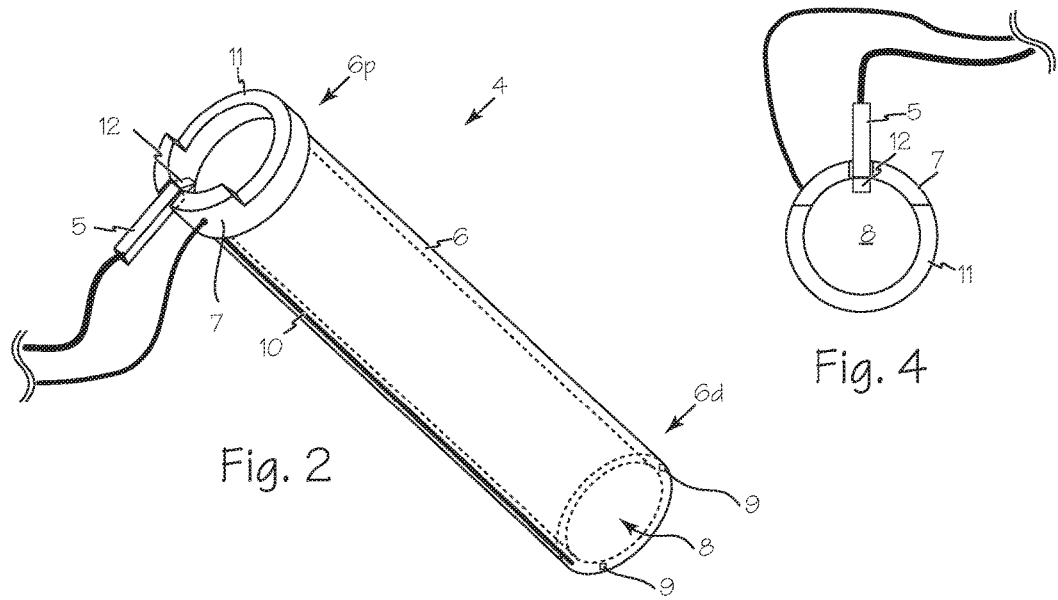
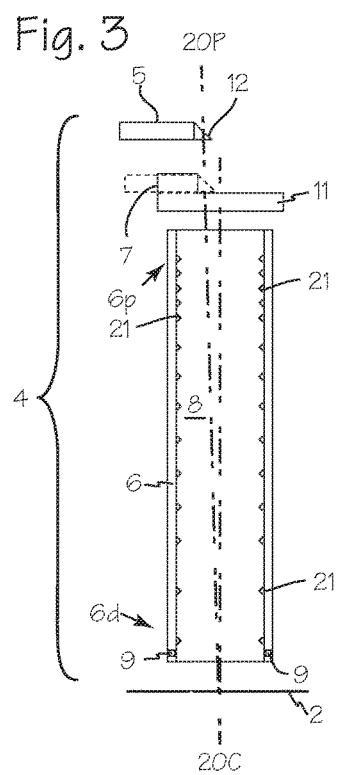
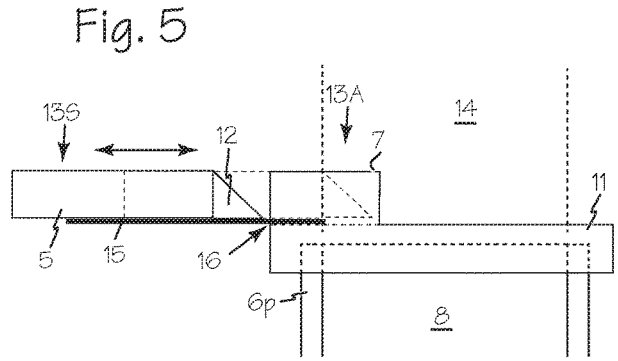
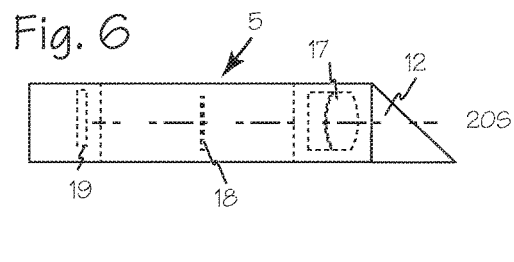

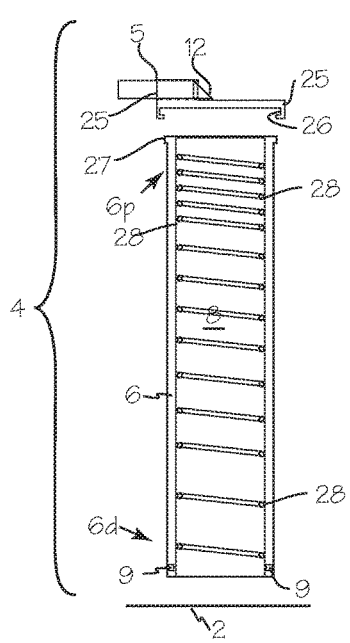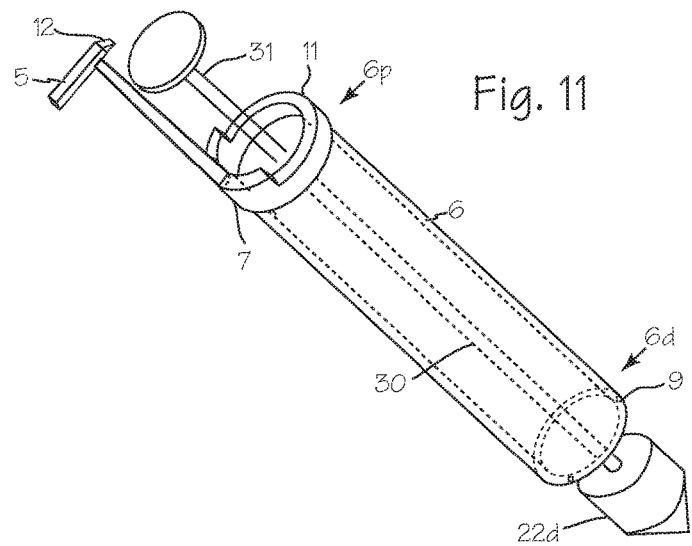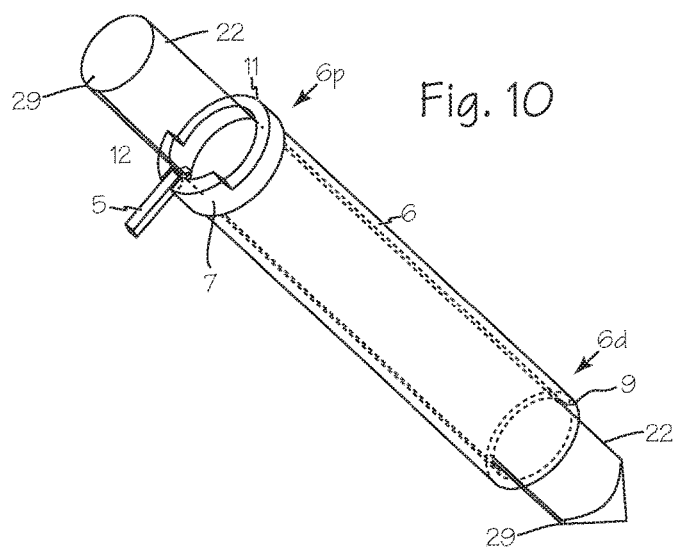

CANNULA WITH PROXIMALLY MOUNTED CAMERA AND TRANSPARENT OBTURATOR

This application is a continuation of U.S. application Ser. No. 15/576,536, filed Nov. 22, 2017, which is the National Stage of International Application PCT/US2017/047424 filed Aug. 17, 2017, which is a continuation-in-part of U.S. application Ser. No. 15/239,632, filed Aug. 17, 2016 and U.S. Provisional Application 62/483,885 filed Apr. 10, 2017.

FIELD OF THE INVENTIONS

The inventions described below relate to the field of minimally invasive brain surgery.

BACKGROUND OF THE INVENTIONS

Stroke is a common cause of death and disabling neurologic disorder. Approximately 700,000 patients suffer from stroke in the United States every year. Hemorrhagic stroke accounts for 20% of the annual stroke population. Hemorrhagic stroke is due to a rupture of a blood vessel in the brain, causing bleeding into the brain tissue and resulting in a hematoma (a blood mass) in the brain. Prompt removal of the blood mass is necessary to limit or prevent long-term brain injury.

Clear visualization and imaging of the blood mass and any surrounding surgical field facilitates removal of the blood mass. Removal and visualization can often be accomplished through a cannula and obturator assembly, placed through a hole drilled in the skull near the site of the hematoma. The site of the hematoma can be accurately identified using a CT scan.

To aid in placement of the cannula and obturator assembly precisely at the hematoma, and also to aid in inserting the cannula through a route least likely to damage healthy brain tissue, neurosurgeons use sophisticated and costly stereotactic surgery systems or neuro-navigation systems. These systems depend on previously obtained MRI or CT scans, which may be several hours old, and thus not perfectly reflective of the shape and location of the blood mass at the time of surgery. In these systems, visual confirmation that the cannula distal end is properly positioned can be accomplished only after the obturator has been removed from the cannula. If the distal end has not been accurately placed, the obturator must be re-inserted, and the cannula and obturator assembly must be manipulated, perhaps repeatedly, until, after removal of the obturator, the blood mass is visible.

A less sophisticated method, used before these expensive neuro-navigation systems and stereotactic systems became standard and still used where these systems are not available, involves large craniotomies, exploration and direct visual search for a blood mass, extensive tissue dissection, and invasive instrumentation, all associated with high mortality and morbidity.

SUMMARY

The devices and methods described below provide for improved visualization of the brain during minimally invasive surgery. The device comprises a cannula with a camera mounted on the proximal end of the cannula with a view into the cannula lumen and the tissue within and below the lumen. A prism, reflector or other suitable optical element is oriented between the camera and the lumen of the cannula to afford the camera a view into the cannula while minimizing obstruction of the lumen.

The devices including the cannula with a camera mounted on the proximal end of the cannula with a view into the cannula lumen and the tissue within and below the lumen, and optionally a display to display images obtained by the camera, can be used with an obturator comprising a long, small cross-section shaft with a short, large diameter tip which is transparent or translucent. The prism, reflector or other suitable optical element is oriented between the camera and the lumen of the cannula to afford the camera a view of the obturator tip while minimizing obstruction of the lumen. The assembled cannula, camera and obturator can be inserted into the brain of a patient, with the obturator tip used to gently dissect brain tissue to make way for the assembly, as well as obturate (occlude) the distal opening of the cannula. The small cross-section obturator shaft is much smaller than the inner diameter of the cannula, affording a sizable annular or circular space between the shaft and the cannula wall to provide good visibility (from the camera) of the proximal surface of the obturator tip. Lights, if necessary, may be provided in the cannula to illuminate the distal end of the obturator tip and cannula or tissue near the distal end of the cannula (lighting may instead be provided from a source outside the assembly, or from lights mounted on the proximal end of the cannula or any combination of the foregoing). Light reflected by tissue near the distal surface of the obturator tip passes through the obturator and out of the proximal surface of the obturator tip, so that a surgeon inserting or manipulating the assembly can easily see that the obturator tip is near brain tissue (which is white to gray) or blood (which is red to black).

The system, and the method of access it enables, may be used as an adjunct to neuro-navigation to help confirm successful navigation to a hematoma, especially where the goal of the surgery is removal of the blood mass through the cannula. The system and the method it enables may be used to locate a blood mass, in lieu of a neuro-navigation system, in situations where the approximate location of the hematoma is known from imaging, or in situations where the approximate location of the hematoma may be ascertained with smaller probes, or during emergent surgery.

BRIEF DESCRIPTION OF THE DRAWINGS

FIG. 2 illustrates a cannula with a proximally mounted camera.

FIG. 3 is an exploded side view of a cannula with a proximally mounted camera.

FIG. 4 is a top view of a cannula with a proximally mounted camera.

FIG. 5 is a close-up side view of a cannula light shield with the camera movable on a track.

FIG. 6 is a close-up side view of the camera for a cannula with a proximally mounted camera.

FIG. 9 illustrates an additional structure of the cannula which provides for easy attachment and detachment of the camera to the cannula tube.

FIGS. 10 and 11 illustrate the camera and cannula system in which the camera is fixed to the cannula tube, and the obturator is modified to pass the camera even as it encroaches on the space over the lumen of the cannula tube.

DETAILED DESCRIPTION OF THE INVENTIONS

Figure 1:
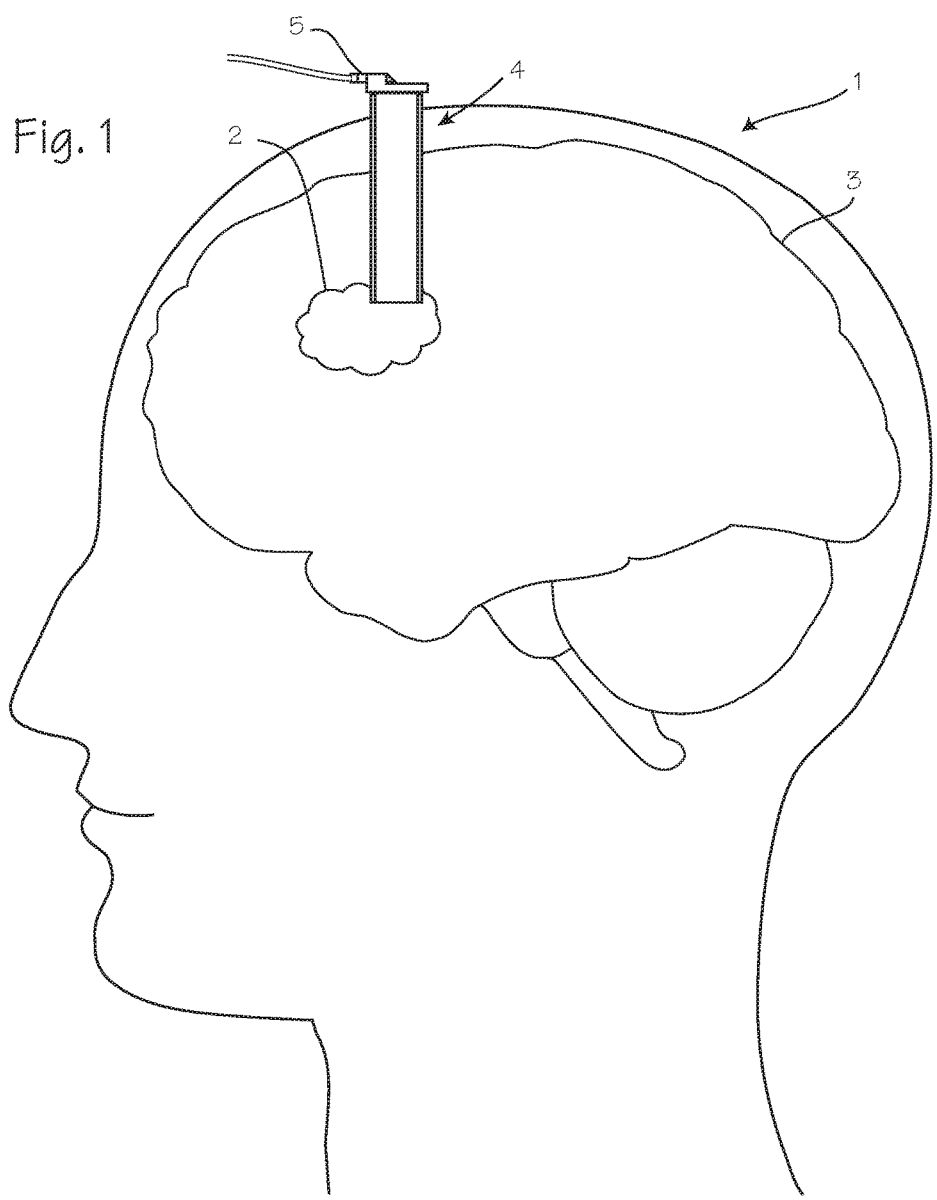
FIG. 1 illustrates the head of a patient with an area requiring surgical intervention.

FIG. 1 illustrates a patient 1 with a blood mass 2 in the brain 3 that necessitates surgical intervention. A cannula 4 has been inserted into the brain, with the distal end of the cannula proximate the blood mass. A camera 5 is mounted on the proximal rim of the cannula, with a portion of the camera overhanging the rim of the cannula and disposed over the lumen of the cannula, and is operable to obtain video or still images of the blood mass or other tissue at the distal end of the cannula.

FIG. 2 illustrates the cannula 4 in detail. The cannula comprises a cannula tube 6, with a distal end 6d adapted for insertion into the body of the patient, and the proximal end 6p which remains outside the body during use. A camera 5 is mounted on the proximal end 6p of the cannula tube. A mounting structure 7 secured to the proximal end of the cannula. The camera, shown in more detail in the following figures, may include or be fitted with a prism, a reflector or other mirror structure or optical element, overhanging the lumen 8 of the cannula tube. If the camera is small compared to the cannula lumen, the camera may be used without the prism or reflector, and may be oriented with its viewing axis aligned along the long axis of the cannula. The light necessary to provide good visualization of the blood mass, and obtain images of the blood mass, may be provided by light sources 9 (LED's or other light source) disposed at the distal end 6d of the cannula tube, at or proximate the distal opening. The light sources may instead be disposed at the proximal end of the cannula tube and the light may be transmitted through the open lumen of the cannula, or may be transmitted through optical fibers 10, or, if the cannula is made of a transparent material, the light may be transmitted down the walls of the cannula tube to exit the distal end of the cannula wall to illuminate the blood mass. The ring 11 of the mounting structure 7 serves as a shield to block light from view from a proximal viewpoint, whether the light emanates directly from proximally located lights, or passes through the cannula tube from distally located lights. In embodiments in which the light sources are disposed on the proximal end of a transmissive cannula tube, the distal portion 6d of the cannula tube may shaped, molded, machined, treated or otherwise configured to enable the emergence of light from cannula tube 6 to illuminate the surgical field. For example, the inner distal surface and/or the outer distal surface may be sanded or frosted or coated to enable emission of light through the surfaces. Where the light sources are disposed toward the distal end of the cannula, the portion of the cannula holding the light sources, and the portion of the cannula distal to the light sources may be optically transmissive to generate more light for the surgical field, while the portion of the cannula proximal to the light sources may be opaque. Cables for providing power to the camera and light source, and carrying image data from the camera to a display, may be provided, or the device may be powered by batteries disposed on the device and image data can be transmitted wirelessly to a display.

FIG. 3 is an exploded side view of cannula 4 with the camera 5 disposed on the proximal rim of the cannula tube, with a prism or reflector 12 overhanging the lumen 8 of the cannula. FIG. 4 illustrates a top view of cannula 4 with a proximally mounted camera 5. FIG. 3 also shows the LEDs 9 disposed on or near the distal end 6P of the cannula tube to emit light into the surgical field (such as blood mass 2).

The camera may be mounted within the mounting structure so that the prism or reflector 12 may be removed from its overhanging position, either by sliding the camera radially, flipping the camera around a pivot, or by removing the camera from the camera mounting structure entirely. FIG. 5 illustrates a sliding attachment of camera 5 to the mounting structure 7 as well as movement of the camera from a standby position 13S to a use position 13A. With camera 5 in use position 13A, the prism/reflector 12 extends partially or fully into the cylindrical space 14 defined by and extending from the lumen 8 and affords an unobstructed view of surgical site at the distal opening of the cannula tube, while providing minimal interference to small diameter surgical instruments using lumen 8 to perform surgery (for example, an aspirator or a macerator). Any suitable technique for moveably attaching the camera 5 to the light shield 7 may be used. For example, the camera may be slidably attached on a track such as track 15, in which case the track 15 secures the camera 5 to the light shield and enables the camera/prism assembly to move radially between a standby position 13S to a use position 13A and back again (that is, from a first position in which the prism extends into the lumen 8 or the cylindrical space 14 defined by the lumen of the cannula tube, to a second position in which the prism resides outside of lumen 8 or the cylindrical space 14 defined by the lumen of the cannula tube). The camera may also be attached with a pivot at 16, so that it is rotatably attached to the tube, from a first position in which the axis of the camera is perpendicular, or substantially perpendicular, to the long axis of the cannula tube to a second position angled from the long axis so that the prism resides outside the cylindrical space 14 defined by a virtual extension of the lumen of the cannula tube. The camera may also be releasably attached to the mounting structure (i.e., it may be readily attached and detached by hand, without the use of tools, during a surgical procedure) with a friction fit or detent arrangement between the camera and a channel of the mounting structure, or other suitable releasable attachment means.

FIG. 6 is a close-up side view of the camera 5. The camera 5 comprises the prism or reflector 12, a lens or lenses 17 (which may include an achromatic lens or other doublet), the imaging device 18 and the control system 19 (if provided in the camera component of the system). The lens 17 may be part of an optical assembly that includes additional optical components. The imaging device 18 may be any suitable image sensor such as a CCD sensor or CMOS sensor. The control system 19 may include a controller, data processing components and transmitters such as a controller and a transmitter to control the camera and transmit data from the camera (the data output system may be located off the device). Suitable cables or wireless transmitters may be used to connect the camera to a display system and a power supply. The imaging sensor is characterized by an imaging plane, and the prism is aligned with the imaging plane to direct light directed parallel to the imaging plane toward the imaging plane. As illustrated, the imaging plane is parallel to the long axis of the cannula tube, and the prism/reflector is disposed along a line perpendicular to the imaging plane, and is oriented to direct light from the surgical field at the distal end of the cannula tube onto the imaging plane.

In the illustrated embodiment, a central longitudinal axis 20L extends concentrically throughout the length of the tubular body. The imaging sensor has an imaging sensor axis (a primary viewing axis) 20S, extending at a perpendicular to the sensor surface and intersecting a radially facing surface of the prism. As illustrated, the central longitudinal axis and the imaging sensor axis intersect at about a 90° angle. In alternative configurations, the angle is within the range of from about 70° and 110°, or within the range of from about 85° and 95°. The angle may be greater than or less than 90° depending upon the desired configuration.

In any of the embodiments disclosed herein, a prism viewing axis 20P (a secondary viewing axis, which is the line of sight through the cannula, from the prism to the distal end of the cannula) intersects a distal surface of the prism, and extends axially distally through the tubular body toward target tissue. In some implementations the prism viewing axis intersects the central longitudinal axis of the cannula at about the distal end of the cannula, or within about 4 cm or 2 cm or less from the distal end of the cannula. The prism overhangs the cannula lumen by no more than about 25% of the inside diameter of the lumen, generally by no more than about 15% or 10% or less of the inside diameter of the lumen. For this reason, the secondary viewing axis typically resides at an angle to the central longitudinal axis. Depending on the type of prism used, the prism viewing angle may be perpendicular to the distal optical surface of the prism (for a reflective, right angle prism shown in the figures, in which the long surface is used as the roof, for example), and the prism may be disposed over the cannula lumen such that the distal optical surface is tilted slightly, relative to the transverse plane of the cannula, to aim the prism viewing axis at the desired point, such as an intersection with the central longitudinal axis of the cannula at the distal end of the cannula. For other reflective and deflective prisms for which the viewing angle is not perpendicular to the distal optical surface, the distal optical surface can be angled, as appropriate, to aim the prism viewing axis at the desired point such as an intersection with the central longitudinal axis of the cannula at the distal end of the cannula. Various forms of prisms may be used, including a pentaprism, half pentaprism (a non-inverting and non-reverting prism which bends light 45° from the prism viewing axis, so that the imaging sensor viewing axis may be disposed at about a 45° angle to the prism viewing axis or the cannula longitudinal axis), a Schmidt prism (an inverting and reverting prism which bends light 45° from the prism viewing axis, so that the imaging sensor viewing axis may be disposed at about a 45° angle to the prism viewing axis or the cannula longitudinal axis), Porro prisms (an inverting and reverting prism which displaces the light entering the prism to an offset but parallel path, so that the imaging sensor viewing axis may be parallel to but radially displaced from to the prism viewing axis or the cannula longitudinal axis) or other prisms, or combinations or configurations of prisms (and Amici/Penta prism combination, for example, or a right angle prism disposed with the long surface facing distally, so that the right angle surfaces serve the reflecting surfaces to redirect the image along an anti-parallel path to the prism viewing axis, optionally paired with a second right angle prism to redirect the image to a parallel but offset path, or a Bauerfeind prism), operable to reflect or displace light from the distal end of the cannula toward the imaging sensor.

In embodiments in which illumination is provided by lights disposed on the distal end of the cannula tube, any resultant glare and reflections from the inner wall of the cannula tube can be minimized by providing baffles on the interior wall of the tube. The baffles may comprise ridges protruding slightly into the lumen, dispersed along the length of the tube. Preferably, the ridges are progressively spaced, such that they are more closely spaced toward the proximal end of the tube, and relatively more widely spaced toward the distal end of tube. Several such ridges are illustrated in FIG. 3, marked as item 21. The ridges may be provided in any form, and may be integral to the cannula tube 6 (for example, formed during molding) or may be glued or fused onto the inner wall of the tube, or they may comprise turns of a coil, or turns of a braid, inserted into the tube or fused into the inner wall of the tube, and the coil or braid can comprise power or data cables associated with the distally located lights or distally located cameras or sensors.

Figure 7:
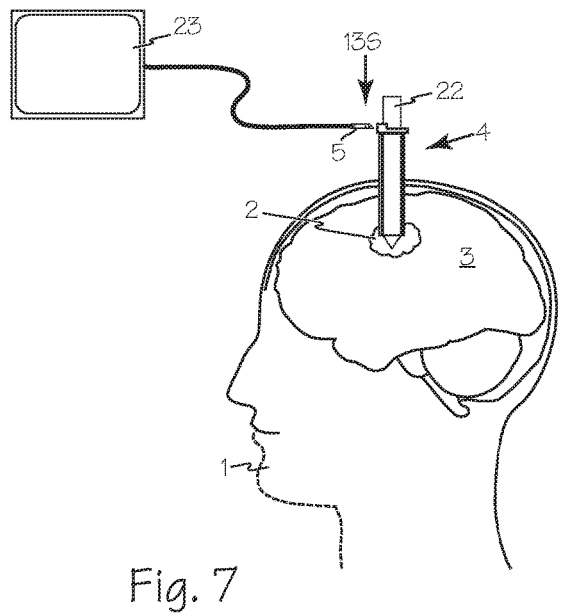
FIG. 7 illustrates the insertion of an obturator and cannula with a proximally mounted camera into a tissue mass in the patient of FIG. 1.
Figure 8:
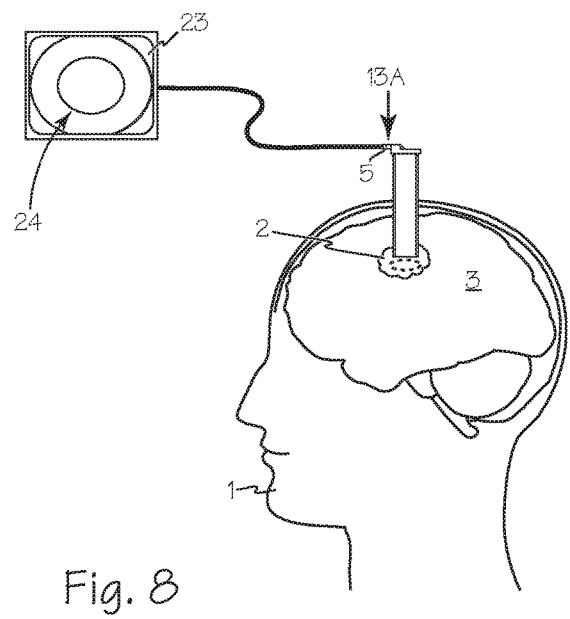
FIG. 8 illustrates the use of a cannula with a proximally mounted camera to perform minimally invasive surgery on the patient of FIG. 1.

As shown in FIGS. 7 and 8, a surgeon inserts the cannula 4 with an obturator 22 into the patient's brain until distal end 6d of the cannula is sufficiently close to tissue 2 for surgery. The surgeon then removes the obturator 22 so that the cannula 4 can be used to provide access, illumination and visibility for the surgical field. The surgeon then moves camera 5, shifting, rotating, or moving it, depending on the construction, from a standby position to place the prism over the lumen. If necessary, the surgeon orients the imaging system to obtain a view of the surgical field. With the camera in place, the surgeon operates the camera to obtain an image of the surgical field. Image data from camera 5 is transmitted to the display 23 to provide image or images 24 of the surgical field obtained through lumen 8. The image may include still images (photographs) and video. After placement of the camera, the surgeon may pass surgical instruments, or the distal end of surgical instruments, through the lumen of the cannula, while the portion of the camera is disposed within the lumen 8 or the space 14 over the lumen.

FIG. 9 illustrates an additional structure of the cannula 4 which provides for easy attachment and detachment of the camera 5 to the cannula tube 6. The camera is fixed to the mounting structure 25, and the mounting structure is releasably attachable to the cannula tube. The mounting structure comprises a ring, similar to mounting structure and ring combination shown in the previous figures (items 7 and 11) with first locking element such as a groove 26 on the inside of the ring, and the proximal end of the cannula tube includes a second, complementary locking element such as a flange 27, sized and dimensioned to fit snugly in the groove of the mounting structure. The mounting structure may be snapped onto the cannula, when desired, to position the camera on the proximal end of the cannula tube, with the prism overhanging the wall of the cannula tube and disposed over the lumen 8. The mounting structure is releasably attached, in that it may be readily attached and detached by hand, without the use of tools, during a surgical procedure. Other releasable attachment means, including a friction fit between the mounting structure and the outside or inside wall of the cannula tube, or a magnetic attachment (with paired magnets in the cannula tube proximal end and in the mounting structure), or a snap fitting, or a detent arrangement between the mounting structure and the cannula proximal end, or a threaded fitting (with complementary inside and outside threads on the mounting structure and cannula proximal end, or vice-versa), or a bayonet mount, with complementary slots and pins on the mounting structure and cannula proximal end, or vice-versa, may be used.

Also, FIG. 9 illustrates an alternative embodiment of the baffles shown in FIG. 3. In FIG. 9, the baffles comprise turns of a coil 28. The baffles may also comprise a braid. The coil or braid can also comprise the electrical wires needed to carry power to the lights disposed on the distal tip of the cannula tube, or a sensor disposed on the distal tip of the cannula tube, and can also comprise data cables needed to transmit data from any such distally mounted sensor to control or display systems associated with the sensors.

FIGS. 10 and 11 illustrate the camera and cannula system in which the camera 5 is fixed (i.e. not releasably attached) to the cannula tube 6, and the obturator 22 is modified to pass the camera even as it encroaches on the space over the lumen of the cannula tube. In FIG. 10, the obturator 22 is essentially isodiametric throughout its length, and has a groove 29 extending along its length (the portion disposed within the cannula tube). The groove is sized and dimensioned to accommodate the prism that overhangs the lumen of the cannula tube. With this construction, the obturator can be inserted into the cannula tube, and the assembled cannula and obturator can be pushed into the brain, while the cannula is in place, fixed to the cannula. In FIG. 10, the obturator 22 comprises a large diameter distal portion 22d, with an outer diameter approximately the same as the inner diameter of the cannula tube, and a small diameter rod 30 that fits easily within the lumen of the cannula tube. The camera is supported on a pylon or post 31. The post holds the camera away from the proximal opening of the cannula tube, at a sufficient distance, compared to the length of the large diameter portion 22d of the obturator, so that the obturator may be tilted or bent in order to insert large diameter portion 22d of the obturator into the lumen without the need to move the camera.

FIGS. 12 through 19 illustrate a cannula, camera and obturator system using a cannula and camera system similar to that illustrated in FIG. 11, with a transmissive obturator tip which allows a surgeon to see tissue beneath the obturator tip while inserting the assembled cannula and obturator into the brain.

Figure 12:
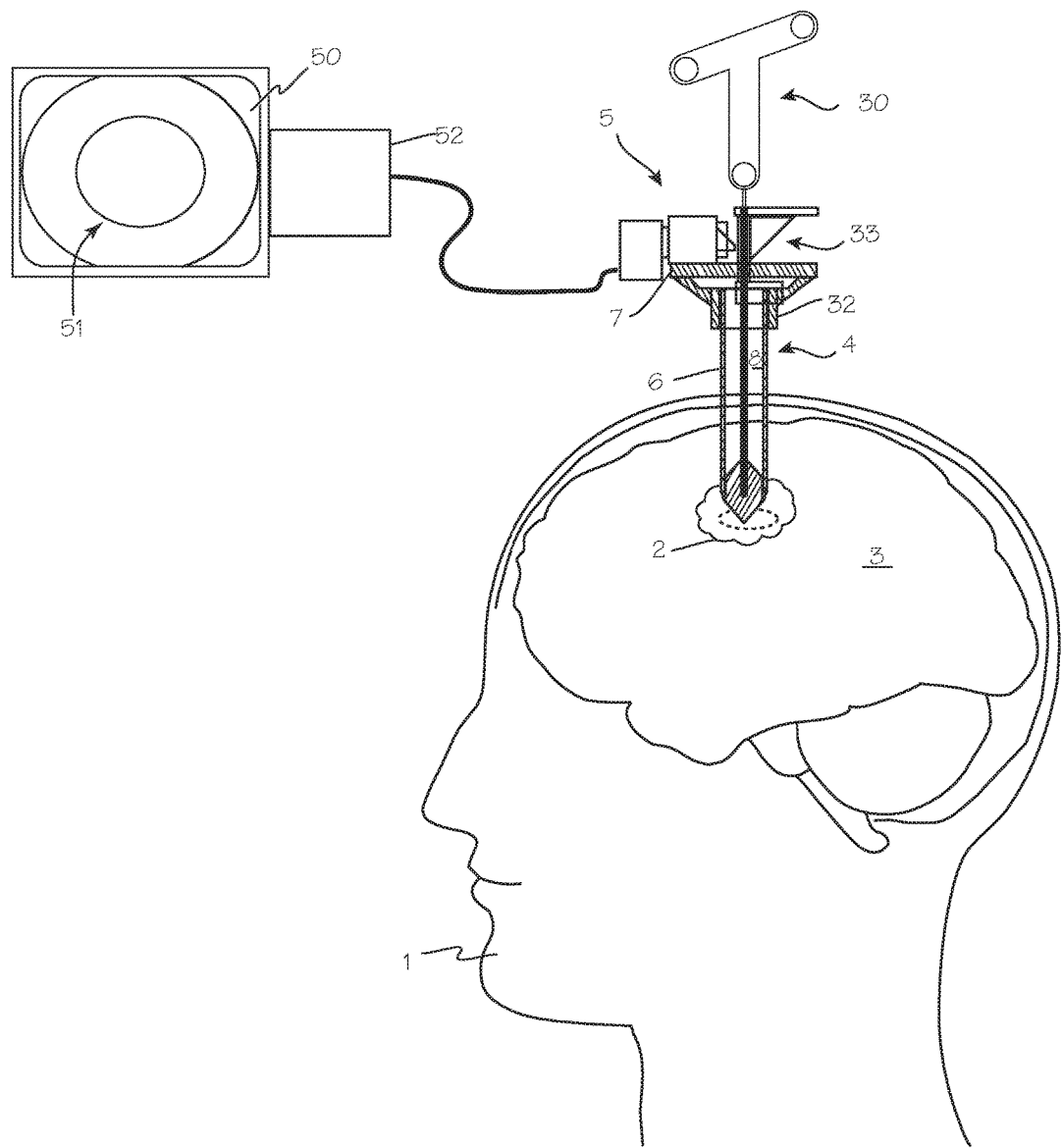
FIG. 12 illustrates a patient with a blood mass in the brain that necessitates surgical intervention, with a cannula which has been inserted into the brain, with the distal end of the cannula proximate the blood mass and an obturator tip extending into the blood mass.

FIG. 12 illustrates a patient 1 with a blood mass 2 in the brain 3 that necessitates surgical intervention, with a cannula 4 which has been inserted into the brain, with the distal end of the cannula proximate the blood mass. A camera 5 is mounted on the proximal rim of the cannula, with a portion of the camera overhanging the rim of the cannula and disposed over the lumen of the cannula, and is operable to obtain video or still images of the distal end of the cannula lumen, which may include images of an obturator tip in the cannula or images of a blood mass, brain tissue, cerebrospinal fluid (CSF) or other tissue at the distal end of the cannula. As shown in both FIGS. 12 and 13, the cannula comprises a cannula tube 6 with a camera 5 and one or more light sources and a mounting structure 7 secured to the proximal end of the cannula. The camera includes a prism, reflector or other mirror structure or optical element, overhanging the lumen 8 of the cannula tube. The camera may be permanently fixed to the proximal end of the cannula (meaning that it cannot easily be removed intra-operatively, without tools or destructive disassembly) or releasably attached to the proximal end of the cannula (meaning that it can be readily attached and detached intraoperatively, without the need for special tools or destructive disassembly). A portion of the camera assembly, such as the prism, reflector or mirror, extends into the cylindrical space 14 defined by the lumen of the cannula tube and extending proximally beyond the proximal end of the cannula, and is spaced from the proximal end of the cannula, and extends only slightly into the cylindrical space 14 (by no more than about 25% of the inside diameter of the lumen, preferably no more than about 15% or 10% of the inside diameter of the lumen) so that the obturator tip, when sized and dimensioned relative to the proximal spacing of the camera assembly and the intrusion of the camera assembly component into the cylindrical space 14, may be tilted to avoid the intruding camera assembly component and pushed into the proximal end of the cannula. The camera may include a simple focusing means, such as a thumbscrew or slidable post 32 operable by hand to move the imaging sensor radially inwardly or outwardly to adjust the focus of the camera to different depths within the cannula or beyond the distal end of the cannula.

The light necessary to provide good visualization of the blood mass, and obtain images of the blood mass, may be provided by lights 9 (LED's or other light source, shown in FIG. 13) disposed at the distal end 6d of the cannula tube, at or proximate the distal opening. The cannula itself is preferably opaque, and non-reflective, or coated with an anti-reflective coating. The LED's may instead be disposed at the proximal end of the cannula tube and the light may be transmitted through optical fibers, or, if the cannula is made of a transparent material, the light may be transmitted down the walls of the cannula tube to exit the distal end of the cannula wall to illuminate the blood mass. The ring 11 of the mounting structure 7 may serve as a shield to block light from view from a proximal viewpoint, whether the light emanates directly from proximally located lights, or passes through the cannula tube (if transparent) from distally located lights. A prism, reflector or mirror 12 overhanging the lumen 8 of the cannula allows the camera to view down the long axis of the cannula, if the camera is large such that it must be mounted with its viewing axis perpendicular to the long axis of the cannula. In embodiments in which the light sources are disposed on the proximal end of the cannula tube, the distal portion 6d of the cannula tube may be shaped, molded, machined, treated or otherwise configured to enable the emergence of light from cannula tube 6 to illuminate the surgical field. For example, inner distal surface and or outer distal surface may be sanded or frosted to enable emission of light through the surfaces. Cables for providing power to the camera and light source, and carrying image data from the camera to a display, may be provided, or the device may be powered by batteries disposed on the device and image data can be transmitted wirelessly to a display.

Figure 13:
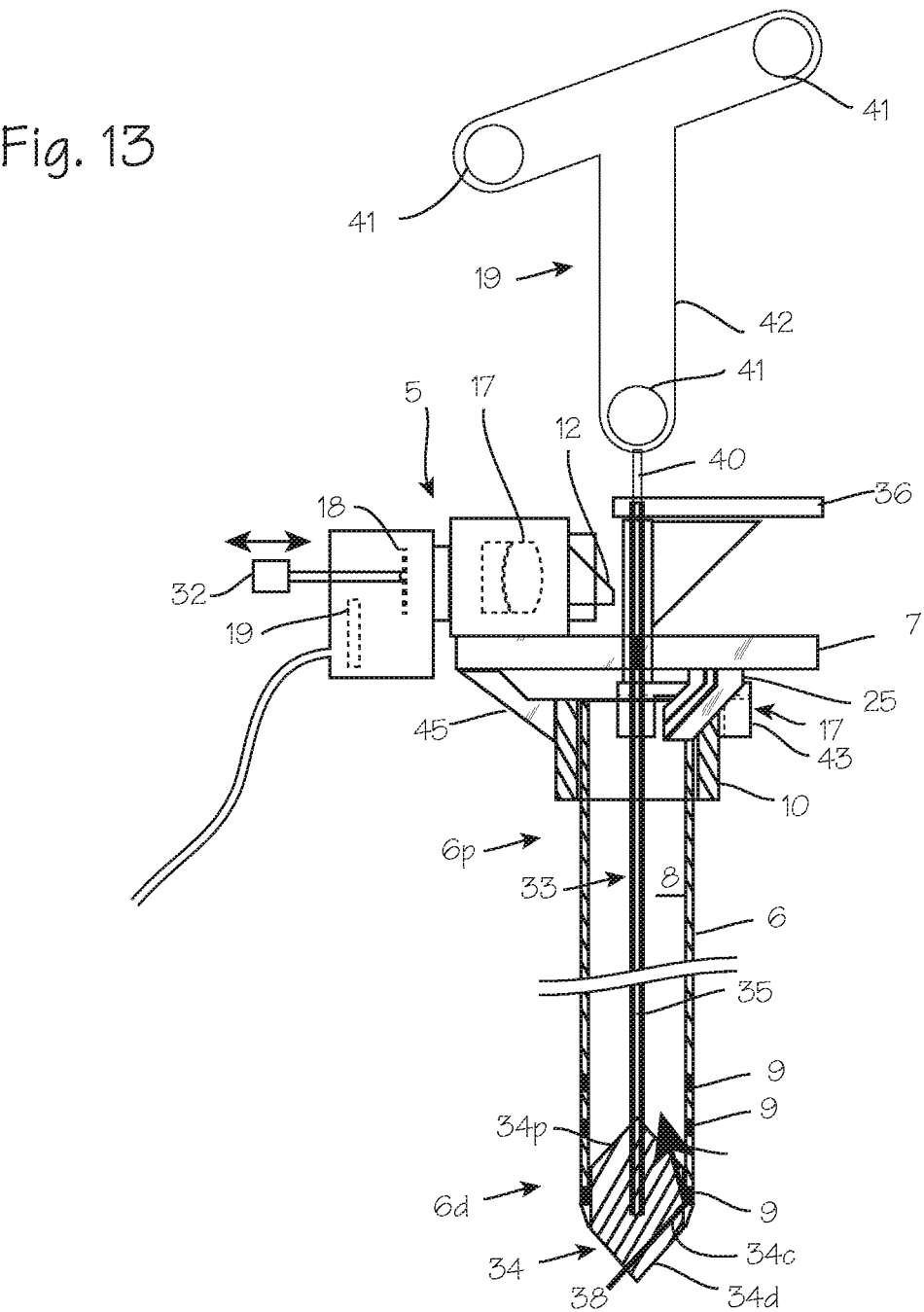
FIG. 13 illustrates a cannula, camera and obturator system.

FIG. 13 also illustrates the obturator 33. The obturator comprises the obturator tip 34, shaft 35, handle 36, and mounting structure 37. The obturator tip is a solid structure with a conically convex distal surface 34d, a conically convex proximal surface 34p, and an axially short circumferential surface 34c. The tip, in the region of the circumferential surface, has an outer diameter (a transverse diameter, along a plane perpendicular to the long axis of the cannula, and corresponding to the transverse cross sectional diameter of the cannula) that closely matches the inner diameter of the cannula, but allows easy longitudinal translation of the tip through the lumen of the cannula. The tip, configured as shown in FIG. 13, will act as a lens, such that light rays (represented by arrows 38) are refracted through the tip, and bent such that any "image" passing through the tip, when formed as illustrated, may be reversed. The tip may have a rectilinear longitudinal cross section, with a central cylindrical portion and distal and proximal conical portions, as illustrated, or a more rounded cross section. The shape illustrated in the Figures may be described as a dual-ended conical spheroid, but the tip may also be a sphere, a spheroid, a prolate spheroid (a football, rugby ball), and oblate spheroid, or an ovoid (egg-shaped). The distal taper preferably ends in an acutely pointed tip which is preferred for use in the brain, but may terminate in a blunt or rounded tip. The distal surface and proximal surface need not be symmetric about the longitudinal axis, or symmetric about a transverse axis. For example, the distal surface may be pointed, with a rectilinear cross section, while the proximal surface is pointed, rounded, or flat.

The obturator tip is optically transmissive, not optically opaque, and may be optically transparent or optically translucent. The transmittance of the tip need only be adequate, in the visible spectrum, to pass the color of tissue in contact with the distal surface, given the brightness of any illumination provided by the light sources, to provide enough transmitted light to the camera and/or eye of the surgeon to allow the color of tissue around the tip to be discerned from light transmitted through the proximal surface of the tip. The tip may be made of glass, silica, acrylic, polycarbonate, silicone, nylon, polyamides or copolymers or any other material suitable for use in a medical device. The obturator tip surface may be polished or frosted. The obturator tip may optionally comprise radiopaque substances (elements or compounds such as platinum particles, for example) to render the tip radiopaque, so that it appears distinctly under fluoroscopy during surgery. The obturator tip may optionally comprise sensors such as pH sensors, impedance sensors, force sensors, glucose sensors, etc., to assist in detecting a blood mass or CSF and distinguishing them from surrounding brain tissue.

The proximal surface of the tip, which tapers to a small diameter in the proximal direction, also provides for clearance of the tip when the obturator must be removed to make room for other devices. As shown on FIG. 14, the convex surface allows for clearance from the camera, with a slight tilt of the obturator shaft away from the longitudinal axis of the cannula, so that removal of the obturator is not blocked by the overhanging prism of the camera assembly.

The shaft 35 may be a solid rod or a tube, with a small diameter, or transverse cross section, compared to the cannula lumen, so that the tip proximal surface can be viewed from the cannula proximal end. If provided as a tube, the lumen of the shaft may accommodate a neuro-navigation stylet or probe 39 with passive markers detectable by the neuro-navigation system, useful for guidance of the assembly into the brain. The rod 40 of the neuro-navigation stylet may be inserted into the lumen of tubular shaft, as shown, so that the assembled cannula, obturator and stylet may be tracked by a neuro-navigation system, through tracking of the markers 41 on a frame 42 to aid in accurate placement of the distal tip of the assembly. The shaft 35 may also accommodate a neuro starburst connection. The shaft need not be circular, and may have a square or oval cross section, so long as the shaft transverse cross section is small compared to the cannula inner diameter so that the tip proximal surface can be viewed from the cannula proximal end. The shaft may alternatively comprise a half-pipe, with an outer diameter closely matching the inner diameter of the cannula, with the half-pipe arranged opposite the camera assembly, leaving a large portion of the cannula lumen clear for visualization of the tip from the proximal end of the cannula.

The obturator mounting structure 37 includes a depending rim 43, with a keyway 44 (see FIG. 14) sized to friction fit over a strut 45 or other structure of the camera mount or cannula rim or other component. Any other suitable mating means, such as a notch in the cannula and a matching rail in the mounting structure, or a depending pin or rim on the mounting structure which fits into a hole or circumferential channel in the cannula, may be used. The mating means also preferably serves to limit the longitudinal travel of the obturator relative to the cannula, such that when the mating means is secured to the cannula, the obturator distal surface protrudes from the distal end of the cannula. The mating means, such as the keyway or notch, may also serve as a means for registering the rotational position of the tip, should it be desirable to provide an index indicia on the tip, to assist a surgeon in identifying the location of features discernable through the tip, relative to structures on the proximal end of the assembly.

The camera 5 comprises the prism 12, a lens or lenses 17 (which may include an achromatic lens or other doublet), the imaging device 18 and the control system 19 (if provided in the camera component of the system). The lens 17 may be part of an optical assembly that includes additional optical components. (For example, a stenopeic aperture may be positioned in the light path between the prism and the sensor, preferably between the prism and the lens. This may be accomplished by mounting a sheet or applying a mask to the proximal surface of the prism, containing an aperture having a diameter within the range of from about 1.0-2.0 mm and in one embodiment about 1.5 mm.) The imaging device 18 may be any suitable image sensor such as a CCD sensor or CMOS sensor. The control system 19 may include a controller, data processing components and transmitters such as a controller and a transmitter to control the camera and transmit data from the camera (the data output system may be located off the device). Suitable cables or wireless transmitters may be used to connect the camera to a display system and a power supply. The imaging sensor is characterized by an imaging plane, and the prism is aligned with the imaging plane to direct light rays traveling through the cannula lumen substantially in parallel or at a non-parallel angle to the imaging plane toward the imaging plane. As illustrated, the imaging plane is parallel to the long axis of the cannula tube, and the prism disposed along a line perpendicular to the imaging plane, and oriented to direct light from the surgical field at the distal end of the cannula tube onto the imaging plane.

Figure 14:
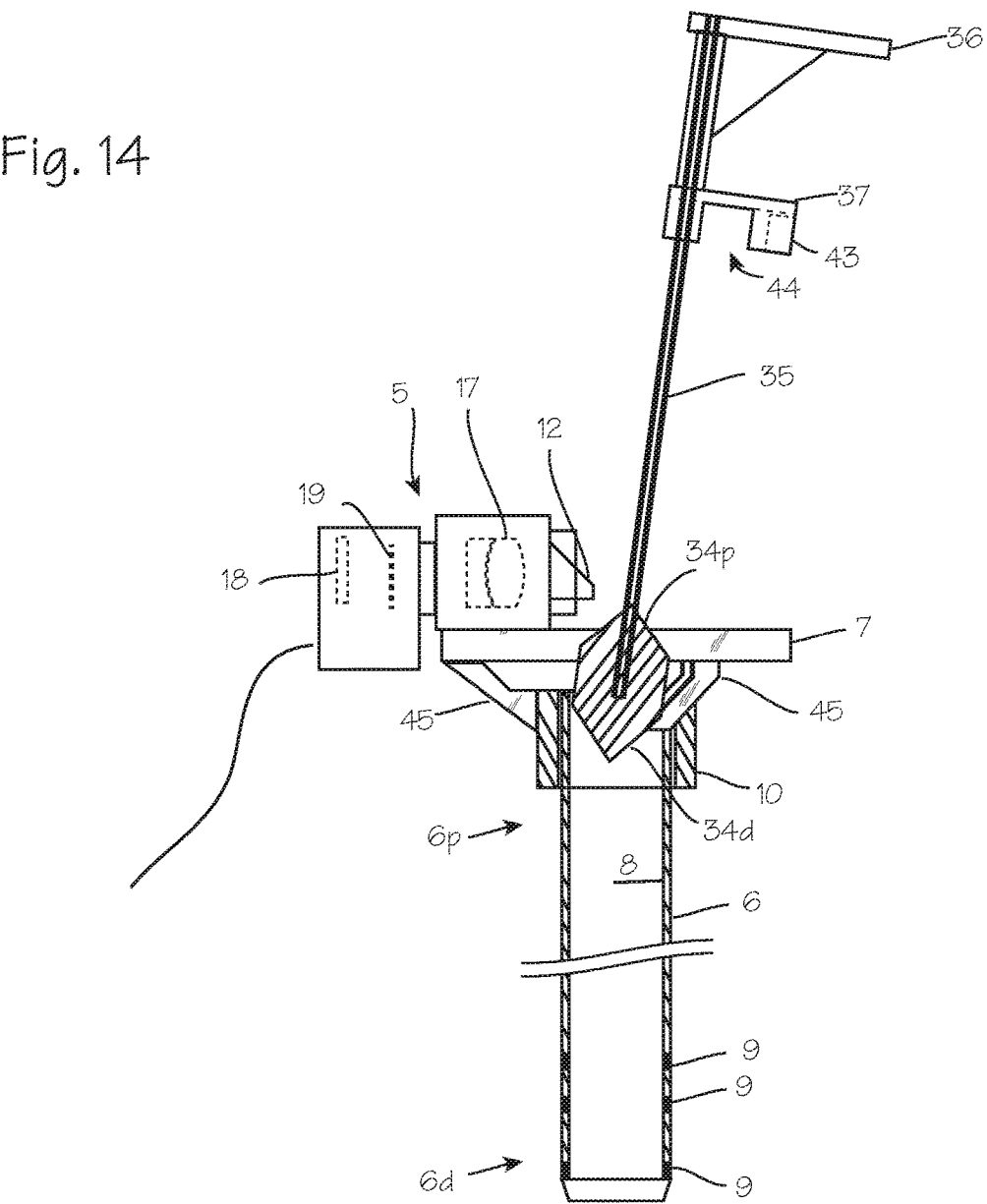
FIG. 14 illustrates removal of the obturator while the camera assembly remains fixed to the proximal end of the cannula.

FIG. 14 illustrates removal of the obturator while the camera assembly remains fixed to the proximal end of the cannula. As shown in FIG. 14, the tapered proximal surface of the tip allows for removal of the obturator, while the camera/prism assembly is in place and overhanging the lumen of the cannula. The obturator may simply be tilted away from the long axis of the cannula to clear the camera and prism. If the proximal surface of the tip is not tapered, the camera assembly may be removed momentarily to clear the cylindrical space over the lumen to allow removal of the obturator.

As shown in FIG. 13, a surgeon inserts the cannula 4 with an obturator 33 into the patient's brain until the distal end 6d of the cannula is sufficiently close to tissue 2 for surgery. While inserting the cannula and obturator, the surgeon operates the camera and control system to display an image of the cannula lumen and structures at the distal end of the cannula on a display. Image data from camera 5 is transmitted to the display 50 to provide an image or images 51 of the structures at the distal end of the cannula through lumen 8 and the proximal surface of the obturator tip. The display may be operated by a control system which is operable to receive image data from the camera, transmit the image data to the display, and also add additional images to the display such as markers, cursors, and indicia of patient data. If the cannula lumen is large, the surgeon may directly view the proximal surface of the obturator tip to view the brain or blood proximate the distal surface of the obturator tip.

Figure 15:
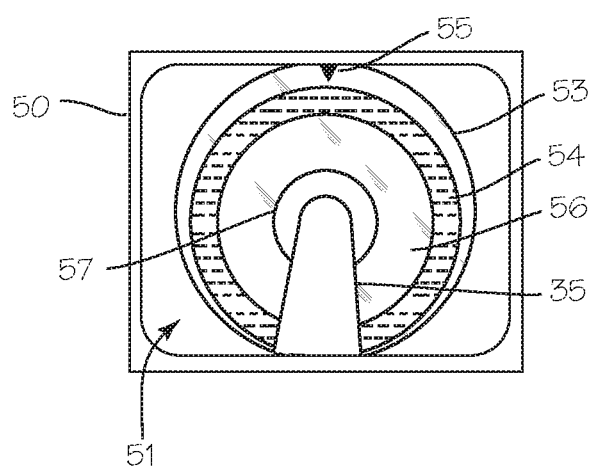
FIGS. 15, 16 and 17 depict exemplary images obtained by the camera while advancing the system through the brain.
Figure 16:
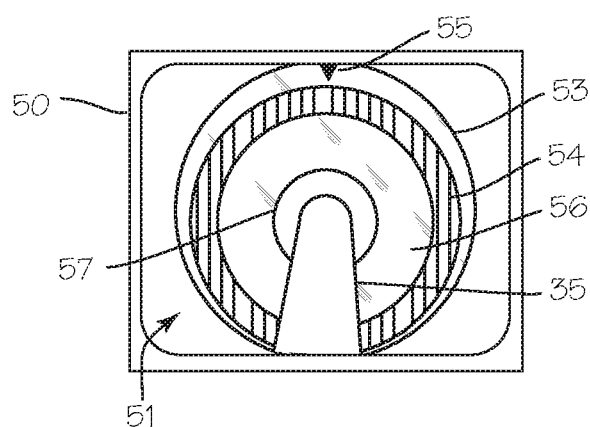
Figure 17:
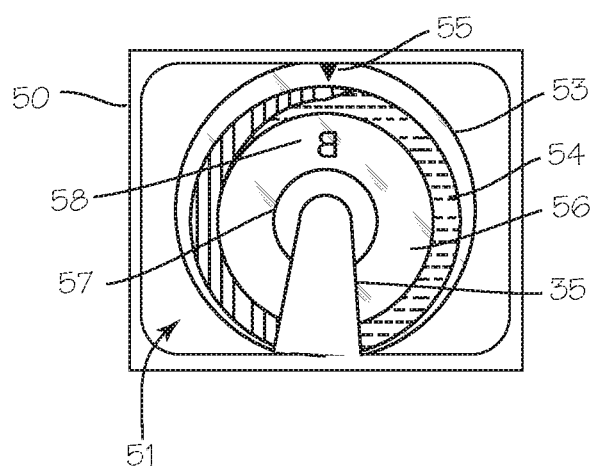

FIGS. 15, 16 and 17 depict exemplary images obtained by the camera while advancing the system through the brain. These are exemplary depictions of what a surgeon would see while pushing the distal tip of the obturator, while disposed within the cannula with the distal surface of the obturator extending distally from the distal edge of the cannula, through the brain and toward a blood mass. These images correspond to an insertion toward a blood mass that is somewhat deep in the brain, below a layer of healthy brain tissue. Upon initial insertion into the brain, while the tip is passing through healthy brain tissue, the surgeon will see an "image" of the healthy brain tissue, which appears white or off-white (various shades of ivory, bone, linen, etc.). Each image includes an image of the obturator shaft 35 and the obturator tip proximal surface 34p, and a portion of the cannula wall surface 53. The image will appear as a ring 54 or partial ring, around an outer peripheral portion of the tip proximal surface. A marker 55, corresponding to an index on the cannula or obturator or a predetermined position relative to the camera, with or without an index, may be inserted into the display by the operating software, to inform the surgeon of the relationship of the displayed image to the position of the cannula and obturator. The index may, for example, be the circumferential position of camera, and the marker can be imposed on the display in a position opposite the camera (this is the configuration shown), though the marker can be imposed on the display in any predetermined relationship to the index. The index can be any feature of cannula or obturator. These features are depicted in FIGS. 15, 16 and 17. Additional features visible in these views include a bright ring 56 inside the image ring 54, and an epoxy ring 57 used to secure the obturator shaft to the obturator tip.

Upon initial insertion, as the tip enters healthy brain tissue overlying the blood mass, the ring 54 will appear white, and the surgeon will see an "image" of the brain tissue, which appears white (brain colored). As the tip enters the blood mass, the ring 54 will turn red, and the surgeon will see an "image" of the blood mass, which appears as blood red or black. This is depicted in FIG. 16. If the tip is located at the margin of the blood mass, the "image" will include a circumferential portion that is white (brain colored) and a circumferential portion that is red or black (blood-colored), and various shades of both, depending on thickness of any blood between the tip and the brain tissue (for example, for circumferential regions of the distal surface of the tip near the margins of the blood mass, the corresponding image transmitted through the proximal surface of the tip will be pinkish, or a mix of the blood and brain shades. The surgeon can determine the distal margin (relative to the cannula and entry point in the skull) of the blood mass by pushing the tip further into the brain, after entry into the blood mass (as indicated by an image similar to FIG. 16) until an image of brain tissue again appears from the proximal surface of the tip (as indicated by an image similar to FIG. 15). The surgeon can determine the lateral extent of the blood mass (that it, its width along an axis perpendicular to the long axis of the cannula) by tilting the assembled cannula and obturator, to move the tip laterally until an image of brain tissue is visible on one side of the ring 54. This is depicted in FIG. 17. The image will be reversed by the tip as constructed as shown in FIGS. 12 and 13, but may be reversed by the display system, or it may be reversed by a reversing prism or a reversing/inverting prism provided as prism/reflector 12. As shown FIG. 17, a fiducial marker 58 or other indicia may be imposed on the proximal or distal face of the obturator tip. This fiducial marker may be used by the surgeon to determine the angular orientation of the obturator relative to the camera viewing axis, and/or confirm that the image is displayed without reversal (so that the displayed image is actually a reversed image of underlying tissue, as a result of the lensing effect of the obturator tip) or displayed with reversal (so that the image is a proper image obtained after the image has been reversed by the control system, after having been reversed as a result of the lensing effect of the obturator tip) so that it corresponds to the underlying tissue structure. The control system can be programmed such that it is operable to determine the presence or absence of the fiducial marker in the detected image of the proximal surface of the obturator tip, and, upon detection of the fiducial marker, generate a presented image which is reversed vis-à-vis the detected image, and present the presented image on the display, or, upon determining that no fiducial marker appears in the detected image, generate a presented image which is not reversed vis-à-vis the detected image. When the proximal surface image is reversed by the control system, the fiducial marker in a reverse image along with the reverse image of the proximal surface will be displayed, to indicate to the surgeon that the image displayed has been reversed, and is oriented relative to the camera viewing axis so that left, right, up and down on the display corresponds to left, right, up and down relative to the cannula. In the illustrated example, the fiducial marker is the letter B, which is asymmetric, so that reversal is obvious. The fiducial marker may take any form recognizable by the control system, such as a barcode, or a distinctive array of dots, and is preferably asymmetric. The fiducial marker may also be used by the control system, if, in conjunction with the obturator mount, the fiducial marker is placed in predetermined relationship with the camera, to determine the orientation of the captured image and rotate the displayed image so that the displayed image corresponds structural features of the cannula system, and thus assist the surgeon in properly interpreting the displayed image.

Figure 18:
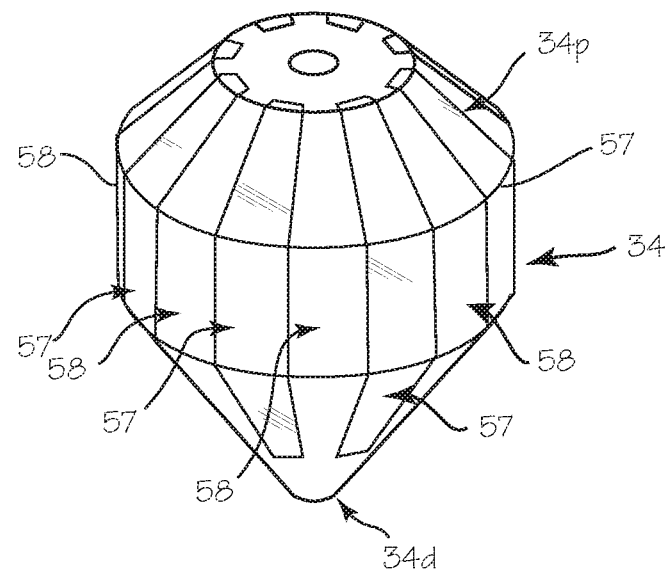
FIGS. 18 and 19 illustrate obturator tips, for use with the cannula, camera and obturator system of FIG. 12.
Figure 19:
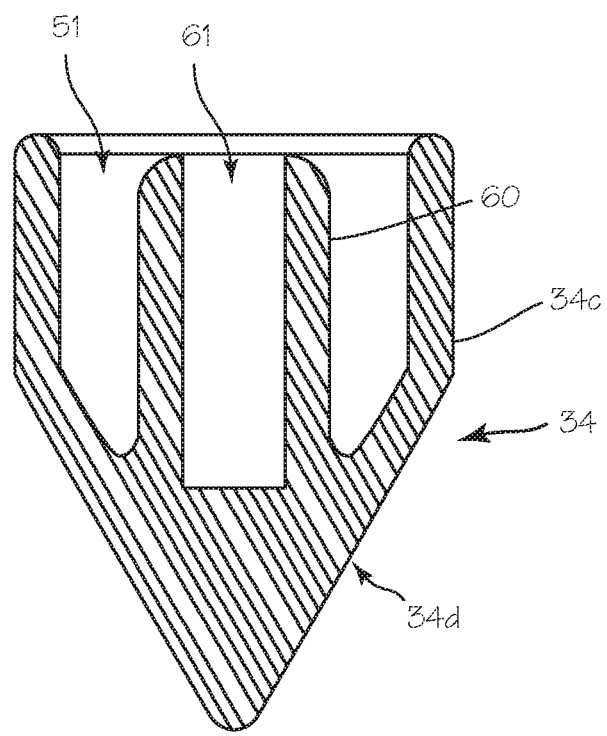

The obturator tip may be configured to avoid image reversal, by providing, with the obturator tip, several longitudinally extending optically opaque structures within the otherwise optically transmissive tip, or by providing several optically transmissive longitudinally extending structures within an otherwise optically opaque tip, to comprise an overall optically transmissive tip through which light from the distal surface is transmitted through the optically transmissive structures (and thus avoids reversal of the single piece structure of FIGS. 1 through 3). This is illustrated in FIG. 18, which shows the obturator tip 34 with a plurality of light transmissive elements 59 extending longitudinally from the distal face 34d, along the circumferential surface 34c, to the proximal face 34p of the obturator tip. These elements may be separated by longitudinally opaque elements 60 extending longitudinally from the distal face 34d to the proximal face 34p of the obturator tip, or they may be discrete elements disposed immediately abutting adjacent discrete opaque elements, such that each light transmissive element transmits light from the distal face to the proximal face without reversal of the overall image. The light transmissive elements may extend to the outer surface of the circumferential surface, as shown, or they may be embedded below the circumferential surface. FIG. 19 illustrates another non-reversing configuration of the obturator tip 34.

This obturator tip includes the conically convex distal surface 34d, an axially short circumferential surface 34c, without the conically convex proximal surface 34p shown in FIG. 13, and includes an annular groove 61, in the proximal surface, extending from the proximal extent of the obturator tip toward the distal surface, between a circumferential wall portion 34w, in the longitudinal region of the circumferential surface and the socket or hosel 62, extending from the distal portion of the tip, with bore 63 into which the obturator shaft (item 35 of FIG. 13) is inserted.

For any of the embodiments disclosed herein, the tubular body may be provided with at least about 4 light sources, and in some implementations at least about 10 or 15 or 20 or 30 or more light sources such as LED's. In one implementation at least about 35 or 40 LED's are carried on the tubular body and exposed to the central lumen. Some or all of the LED's can be right angle LED's.

The light sources may be positioned within about 50% or 30% or 20% or 10% or less of the length of the tubular body from the distal end. In some implementations, the light sources are positioned within about 5 cm or about 3 cm or about 1 or 2 cm from the distal end. The plurality of light sources may reside on a common transverse plane, or a ring of light sources may reside substantially on a common transverse plane (meaning the light sources in that ring may have a small axial position variation but are within about +/−1 cm or 0.5 cm or less of a transverse plane).

The tubular body may be provided with a first, distal ring of light sources positioned distally of a second, proximal ring of light sources. At least a third, intermediate ring of light sources may be positioned in between the first and second rings. The rings may be separated by at least about 2 cm and in some implementations at least about 3 cm or 4 cm or more.

If only a single light source or ring of light sources is provided at the distal end of the tubular body, the light source may become obstructed if blood enters the lumen at the distal end of the tubular body. Providing at least one and preferably two or more secondary light sources spaced axially apart proximally along the length of the lumen allows continuity of light in the event that one or more distal light sources becomes obstructed.

The systems can be configured as a thermally stable system for accessing and imaging an intracranial hemorrhage. When so configured, the device may comprise an elongate tubular body, having a proximal end, a distal end, and a lumen; a plurality of LED light sources carried by the tubular body within about the distal most 30% or 20% or 10% of the length of the tubular body; and a sensor/camera mounted at the proximal end of the tubular body. The lumen accommodates simultaneous viewing of the ICH site while performing procedures on the ICH. Operation of the LED light sources in ambient air at STP for at least 60 minutes at an intensity of at least about 3,000 lumens elevates the distal end of the tubular body by no more than about 22° C. or 17° C. or 10° C. (40° F. or 30° F. or 20° F.). Preferably, operation of the LED's within the range of from about 3500 to about 4500 lumens elevates the distal end of the tubular body by no more than about 22° C. or 17° C. or 10° C. (40° F. or 30° F. or 20° F.). Operation of the device in vivo for an inter-operative time frame needed to treat an ICH (typically 30 to 60 minutes) will preferably elevate tissue in contact with the distal end to a temperature of no more than about 45° C., optimally no more than about 43 or 40° C.

The access and imaging device may comprise at least 3 LEDs and optionally at least about 10 or 20 or 30 LED's within the most distal 30% of the length of the tubular body. The LED's may be positioned in the same transverse plane, or at least one and preferably a plurality of LED's in each of a first and second and optionally third or fourth transverse planes spaced axially apart along the length of the tubular body. At least one and preferably a plurality of the LED's are right angle LED's. At least one LED operates at a wavelength of from about 300 nm to about 1 mm, preferably within the range of from about 390 nm to about 700 nm. A first set of LED's may operate at a first wavelength in the visible range, and a second set of LED's may operate at a second, different wavelength, such as in the infrared range. Alternatively, at least one and preferably a plurality of LED's are tunable between the first and second wavelengths.

The access and imaging device may additionally comprise an optical element carried by the proximal end and positioned within an optical path between the sensor and the distal end. The optical element may comprise a prism, a mirror or other reflector, having a distally facing surface. The central lumen may have a longitudinal axis extending concentrically therethrough; the imaging sensor has a primary viewing axis; and the longitudinal axis and the primary viewing axis intersect at the optical element at an angle. The angle is greater than zero degrees and in some implementations may be within the range of from about 70° and 110°, or within the range of from about 85° and 95°. The prism bends light rays propagating proximally through the tubular body and directs them laterally to the sensor.

The distal surface of the prism overhangs the central lumen by no more than about 25% of the inside diameter of the lumen, preferably no more than about 15% or 10% of the inside diameter of the lumen. The prism may be rigidly mounted or adjustably mounted with respect to the tubular body. A prism viewing axis (the secondary viewing axis) extends at a perpendicular to the distal optical surface of the prism, and the prism viewing axis is non-parallel to the central longitudinal axis of the tubular body. The prism viewing axis may intersect the central longitudinal axis at a point spaced apart from the proximal end by a distance within the range of from about 80% and 120% of the length of the tubular body and preferably at a point spaced apart from the proximal end by a distance within the range of from about 95% and 105% of the length of the tubular body.

The sensor may capture images in either or both the visible and at least one non-visible wavelength, such as infrared. Alternatively, a first sensor with sensitivity in the visible and a second sensor with sensitivity in the infrared may be provided. A beam splitter may be provided to direct reflected light to each of the two sensors. The sensor may be provided with control circuitry, for providing control of digital zoom, contrast, brightness, saturation, sharpness, white balance, and horizontal and vertical alignment and rotation.

The systems can be configured as self-contained medical visualization and access devices. When so configured, the device may comprises an elongate tubular body, having a proximal end, a distal end, and a working channel extending therethrough; and a sensor carried by the proximal end and configured to capture image data propagated in free space through the working channel, where the relationship between the sensor and the working channel is fixed, and manipulation of surgical tools and visualization may be simultaneously accomplished through the working channel. That is, the surgeon can insert a tool, such as a aspirator or macerator, without having to remove the camera to make way for the tools, and continue viewing a display of an image obtained by the camera while manipulating the tool tips within the surgical field at or beyond the distal end of the cannula. The device may further comprise an optical element such as a prism, mirror or other reflector for directing image data from the working channel laterally to the sensor. A secondary viewing axis (from the prism distal face to the distal end of the cannula) extending distally from the prism through free space in the working channel intersects a central longitudinal axis of the working channel at a point that is at least about 75% of the length of the tubular body from the proximal end. A self-contained medical visualization and access device may also further comprise a plurality of LED's within the working channel as described previously.

Any of the foregoing devices may additionally be provided with glare reduction optimization. For example, the central lumen may be provided with a plurality of optical baffles in between a distal light source and the proximal end to inhibit glare from reflected light from the light source in a proximal direction. At least 3 and preferably more light sources are carried by the interior wall of the tubular body, positioned within about 50% and preferably within about 20% of the length of the tubular body from the distal end. The optical baffles may comprise a polarizing grating, which may be carried by the light source and/or carried adjacent the sensor. Alternatively, the optical baffles may comprise a mechanical surface structure on the interior wall such as a plurality of axially spaced apart ridges or grooves or a surface texture which dissipates reflection. The mechanical surface structure may comprise a helical ridge or channel, or discrete circular rings surrounding the central lumen and spaced axially apart. A helical ridge may be formed integrally with the tubular body, or by introducing a helical structure such as a spring into the central lumen.

Any of the foregoing may be provided with a focus and/or depth of field adjustability by moving optical components along an axis other than the central longitudinal axis, thereby optimizing access to the central lumen for use of the obturator or surgical tools and preserving direct line of sight viewing through the central lumen.

For example, the intracranial hemorrhage visualization and access device may comprise an elongate tubular body, having a proximal end, a distal end, and a central lumen. A sensor may be carried by the proximal end, configured to capture focused images of tissue beyond the distal end of the tubular body and within a depth of field. Movement of an optical element radially inwardly or outwardly with respect to the longitudinal axis of the tubular body changes a focal length captured by the sensor. The optical element may be the sensor, or may be a lens.

A prism may be carried by the proximal end and configured to direct an image propagated through free space through the central lumen to the sensor. An optical aperture may be provided in a light path between the prism and the sensor. In some implementations, the aperture has a diameter within the range of from about 1.3 mm to about 1.7 mm. The prism may be immovably secured to the tubular body. The optical system may additionally comprise a lens in the optical path and an adjustment control such as a knob for optical magnification of the target tissue.

Any of the optical elements disclosed herein, at the proximal end of the free space light path extending through the central lumen (e.g., a prism) may have a planar distal optical surface, and a secondary viewing axis extending through the central lumen at a perpendicular to the distal optical surface. The tubular body may be characterized by a central longitudinal axis, and the secondary viewing axis intersects the central longitudinal axis near the distal end of the tubular body, at a point spaced apart from the proximal end by a distance within the range of from about 80% to about 120% of the length of the tubular body; in some implementations within the range of from about 95% to about 105% of the length of the tubular body.

The prism may bend light to an angle within the range of from about 70° to about 110° from the secondary viewing axis (the prism viewing axis) toward the primary viewing axis, and, in some implementations within the range of from about 85° to about 95° from the prism viewing axis. The prism may overhang the central lumen by no more than about 25% of the inside diameter of the central lumen, and preferably no more than about 15% of the inside diameter of the central lumen. The prism may bend light to an angle within the range of from about 70° to about 110° from the secondary viewing axis, and, in some implementations within the range of from about 85° to about 95° from the secondary viewing axis. The prism may overhang the central lumen by no more than about 25% of the inside diameter of the central lumen, and preferably no more than about 15% of the inside diameter of the central lumen.

A feature of the devices described in reference to FIGS. 1 through 9 is the obstruction resistant optical path. Should the system include a distally located optical element (such as a window or lens positioned at or near the distal end of the sheath), the image can become obstructed by blood or other tissue coming into contact with the distal optical surface. This necessitates removal of the device to clear the surface. By positioning the distal most optical surface at the proximal end of the sheath, the optical surface is spaced well apart from the surgical field and the risk of blood or debris contacting the optical surface is minimized. Thus, an enhanced optical performance visualization system for an access device may comprise an elongate tubular body, having a proximal end, a distal end, and a central lumen extending axially therethrough, without an optical element immovably fixed at the distal end of the elongate tubular body (though allowing for the removable obturator shown in FIGS. 12 through 19). An optical system may be provided, comprising a sensor, a lens and a distal most optical surface facing in a distal direction to capture images beyond the distal end of the sheath. The optical surface is spaced apart from the distal end by at least about 80% or 90% of the length of the tubular body such that it is out of range of splashes or debris disrupted by a surgical procedure conducted through the central lumen. In different implementations, the optical surface may be positioned at least about 50 mm and in some embodiments at least about 75 mm or 100 mm or 120 mm or more proximally from the distal end of the sheath.

A feature of the devices described in reference to FIGS. 12 through 19 include the obturator, which is configured for off-axis introduction into the proximal end of the sheath, and the optically translucent distal tip. The obturator may comprise an elongate support and an obturator tip at the distal end of the support. The obturator tip may have a proximal surface which has a tapered surface which tapers radially inwardly in the proximal direction. The proximal surface may be radially symmetric, such as in the shape of a cone. A cylindrical section may extend distally from a distal end of the proximal surface, dimensioned for sliding close fit within the sheath. A distal surface may comprise a conical distal section in which the diameter tapers radially inwardly in the distal direction. Preferably the body is at least translucent and optionally transparent to light such as light in the visible range, though the advantage of off-axis insertion of the obturator may be obtained with an opaque obturator tip, as in FIG. 11. The support may be tubular and may contain electrical or optical conductors such as to operate an infrared mapping sensor carried by the obturator body preferably at the distal end. The distal conical surface is helpful in advancing through soft tissue, while the proximal conical surface facilitates removal of the obturator without the need to displace the prism or other optical element overhanging the central lumen at the proximal end of the sheath.

Thus an intracranial hemorrhage visualization and access system may comprise an elongate tubular body, having a proximal end, a distal end, a central lumen and a longitudinal axis extending therethrough. A sensor carried by the proximal end is configured to capture image data through the central lumen, the sensor having a primary viewing axis. An optical element carried by the proximal end overhangs and extends into the path of a proximal extension of the central lumen. An obturator is axially advanceable through the central lumen. The overhanging optical element interferes with introduction of the obturator into the proximal end of the sheath along the central longitudinal axis of the sheath, but the obturator is configured to enter the proximal end of the sheath along an entry axis that resides at an angle to the central longitudinal axis and then the support may be rotated into parallel or concentric with the central longitudinal axis of the sheath and the obturator may thereafter be advanced axially through the lumen to the distal end coaxially with the tubular body. The axial length of the cylindrical section is less than the distance from the proximal end of the central lumen to the optical element. Thus, the portion of the camera portion of the camera overhanging the lumen is spaced proximally from the proximal end of the cannula to accommodate passage of the obturator tip, and the obturator tip is configured to pass into the cannula lumen while the portion of the camera overhanging the lumen is in place overhanging the lumen.

The obturator tip is preferably sufficiently optically transmissive that color changes beyond the distal surface can be identified by direct visualization of the proximal surface. This enables the clinician to see when the distal surface is in contact with brain tissue, clot or cerebrospinal fluid. In one implementation, the obturator is additionally provided with a sensor such as an IR sensor.

While the preferred embodiments of the devices and methods have been described in reference to the environment in which they were developed, they are merely illustrative of the principles of the inventions. The devices may be used various intracerebral procedures such as intraventricular hemorrhage procedures, neuro-stimulation procedures, and tumor resection. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A cannula system for accessing a blood mass in the brain of a patient, said cannula system comprising:
   a cannula comprising a cannula tube with a proximal end and a distal end and a lumen extending from the proximal end to the distal end; and
   an obturator comprising an obturator shaft having a proximal end and a distal end, and an obturator tip disposed on the distal end of said obturator shaft, said obturator tip being optically transmissive, and having a proximal surface and a tapered distal surface, said obturator being slidable within the cannula tube, and positionable within the cannula tube such that the proximal end of the obturator shaft extends proximally out of the cannula tube proximal end while the tapered distal surface extends out of the cannula tube distal end, wherein the obturator shaft has a transverse cross section smaller than the lumen of the cannula, whereby the proximal surface of the obturator tip is visible from the proximal end of the cannula tube when the obturator tip is disposed within the cannula tube such that the tapered distal surface extends out of the cannula tube distal end;
   wherein the obturator comprises a central cylindrical portion, and distal and proximal conical portions, and said central cylindrical portion has an outer diameter that closely matches an inner diameter of the cannula tube.

2. A cannula system for accessing a blood mass in the brain of a patient, said cannula system comprising:
   a cannula comprising a cannula tube with a proximal end and a distal end and a lumen extending from the proximal end to the distal end; and
   an obturator comprising an obturator shaft having a proximal end and a distal end, and an obturator tip disposed on the distal end of said obturator shaft, said obturator tip being optically transmissive, and having a proximal surface and a tapered distal surface, said obturator being slidable within the cannula tube, and positionable within the cannula tube such that the proximal end of the obturator shaft extends proximally out of the cannula tube proximal end while the tapered distal surface extends out of the cannula tube distal end, wherein the obturator shaft has a transverse cross section smaller than the lumen of the cannula, whereby the proximal surface of the obturator tip is visible from the proximal end of the cannula tube when the obturator tip is disposed within the cannula tube such that the tapered distal surface extends out of the cannula tube distal end;
   wherein the obturator tip comprises a spheroid.

3. A cannula system for accessing a blood mass in the brain of a patient, said cannula system comprising:
   a cannula comprising a cannula tube with a proximal end and a distal end and a lumen extending from the proximal end to the distal end; and
   an obturator comprising an obturator shaft having a proximal end and a distal end, and an obturator tip disposed on the distal end of said obturator shaft, said obturator tip being optically transmissive, and having a proximal surface and a tapered distal surface, said obturator being slidable within the cannula tube, and positionable within the cannula tube such that the proximal end of the obturator shaft extends proximally out of the cannula tube proximal end while the tapered distal surface extends out of the cannula tube distal end, wherein the obturator shaft has a transverse cross section smaller than the lumen of the cannula, whereby the proximal surface of the obturator tip is visible from the proximal end of the cannula tube when the obturator tip is disposed within the cannula tube such that the tapered distal surface extends out of the cannula tube distal end;
   wherein the obturator tip comprises a prolate spheroid.

4. A cannula system for accessing a blood mass in the brain of a patient, said cannula system comprising:

a cannula comprising a cannula tube with a proximal end and a distal end and a lumen extending from the proximal end to the distal end; and an obturator comprising an obturator shaft having a proximal end and a distal end, and an obturator tip disposed on the distal end of said obturator shaft, said obturator tip being optically transmissive, and having a proximal surface and a tapered distal surface, said obturator being slidable within the cannula tube, and positionable within the cannula tube such that the proximal end of the obturator shaft extends proximally out of the cannula tube proximal end while the tapered distal surface extends out of the cannula tube distal end, wherein the obturator shaft has a transverse cross section smaller than the lumen of the cannula, whereby the proximal surface of the obturator tip is visible from the proximal end of the cannula tube when the obturator tip is disposed within the cannula tube such that the tapered distal surface extends out of the cannula tube distal end;

wherein the proximal surface of the obturator tip is tapered.

5. A cannula system for accessing a blood mass in the brain of a patient, said cannula system comprising:

a cannula comprising a cannula tube with a proximal end and a distal end and a lumen extending from the proximal end to the distal end; and an obturator comprising an obturator shaft having a proximal end and a distal end, and an obturator tip disposed on the distal end of said obturator shaft, said obturator tip being optically transmissive, and having a proximal surface and a tapered distal surface, said obturator being slidable within the cannula tube, and positionable within the cannula tube such that the proximal end of the obturator shaft extends proximally out of the cannula tube proximal end while the tapered distal surface extends out of the cannula tube distal end, wherein the obturator shaft has a transverse cross section smaller than the lumen of the cannula, whereby the proximal surface of the obturator tip is visible from the proximal end of the cannula tube when the obturator tip is disposed within the cannula tube such that the tapered distal surface extends out of the cannula tube distal end;

wherein the obturator tip comprises an oblate spheroid.

* * * * *